United States Patent
Pengo et al.

(10) Patent No.: US 9,783,435 B2
(45) Date of Patent: Oct. 10, 2017

(54) METHOD FOR BACTERIA CONTROL, METHOD FOR FUNGI CONTROL, METHOD FOR VIRUS CONTROL, METHOD FOR PREVENTING ENCRUSTATION ON SURFACES AND METHOD FOR PREVENTING CORROSION ON SURFACES

(71) Applicants: Applied.Bio Pesquisa e Servicos em Biotecnologia Ltda., Rio de Janeiro (BR); Edson Renato Pengo, Jaú (BR)

(72) Inventors: Edson Renato Pengo, Jaú (BR); Alane Beatriz Vermelho, Rio de Janeiro (BR); Davis Fernandes Ferreira, Rio de Janeiro (BR); Doneivan Fernandes Ferreira, Rio de Janeiro (BR); Fabrício de Queiroz Venâncio, Rio de Janeiro (BR); Marcelo Adriano Pavanelli Batocchio, Rio de Janeiro (BR)

(73) Assignees: Applied.Bio Pesquisa e Servicos em Biotecnologia Ltda, Rio de Janeiro (BR); Edson Renato Pengo, Jau (BR)

( * ) Notice: Subject to any disclaimer, the term of this patent is extended or adjusted under 35 U.S.C. 154(b) by 0 days.

(21) Appl. No.: 15/178,750

(22) Filed: Jun. 10, 2016

(65) Prior Publication Data

US 2016/0360756 A1     Dec. 15, 2016

(30) Foreign Application Priority Data

Jun. 10, 2015 (BR) .......................... 102015013644-7
Jul. 24, 2015 (BR) .......................... 102015017738-0

(51) Int. Cl.
*A01N 61/02*     (2006.01)
*C02F 1/50*      (2006.01)
*A01N 37/36*     (2006.01)

(52) U.S. Cl.
CPC ................ *C02F 1/50* (2013.01); *A01N 37/36* (2013.01)

(58) Field of Classification Search
CPC ........ A01N 61/02; A01N 37/36; A01N 33/08; A01N 47/10; A01N 47/40; C02F 1/50; C02F 2303/04; C02F 2103/10
See application file for complete search history.

(56) References Cited

U.S. PATENT DOCUMENTS

| | | | | |
|---|---|---|---|---|
| 2008/0305153 | A1* | 12/2008 | Wang | ..... A01N 59/16 424/443 |
| 2015/0105473 | A1* | 4/2015 | Crider | ..... A01N 25/30 514/711 |

FOREIGN PATENT DOCUMENTS

| | | |
|---|---|---|
| BR | 102012009648 A2 | 6/2013 |
| BR | PI0807634 A2 | 6/2014 |
| CN | 102505497 A | 6/2012 |

OTHER PUBLICATIONS

Novak et al (The Journal of the American Oil Chemists' Society, 1961, vol. 38, p. 321-324).*
Si et al (Journal of Applied Microbiology, 2006, 100, 296-305).*
Leonardo, et al., J. Endod. 2001 Dez;27(12):717-9.
Momoh, et al., Bull. Environ. Pharmacol. Life Sci.; vol. 1 [10] Sep. 2012: 21-27.

* cited by examiner

*Primary Examiner* — Sudhakar Katakam
(74) *Attorney, Agent, or Firm* — Laurence P. Colton; Smith Tempel Blaha LLC

(57) ABSTRACT

Methods for organisms control using biocide compositions based on castor oil and/or derivates. In one embodiment, the present invention presents methods of bacteria, fungi, virus and encrustations control. The present invention relates to the fields of Agriculture, Microbiology and Chemical Engineering.

10 Claims, 14 Drawing Sheets

US 9,783,435 B2

METHOD FOR BACTERIA CONTROL, METHOD FOR FUNGI CONTROL, METHOD FOR VIRUS CONTROL, METHOD FOR PREVENTING ENCRUSTATION ON SURFACES AND METHOD FOR PREVENTING CORROSION ON SURFACES

STATEMENT OF RELATED APPLICATIONS

The present patent application claims priority on Brazilian patent application BR 10 2015 013644-7, filed on 10 Jun. 2015 and Brazilian patent application BR 10 2015 017738-0 filed on 24 Jul. 2015.

FIELD OF THE INVENTION

The present invention describes methods for organisms control using biocide compositions based on castor oil and/or derivates. In one embodiment, the present invention presents methods for bacteria, fungi, virus and encrustations control. The present invention relates to the fields of Agriculture, Microbiology and Chemical Engineering.

BACKGROUND OF THE INVENTION

One of the major current challenges of the prior art is providing composition presenting biocide activity (that is, activity against different microorganisms types, such as virus, fungi and bacteria) and being biodegradable at the same time (that is, not generating toxic waste to the environment) and being of low or none toxicity to the environment.

In an aspect of the prior art related to the matter is the issue of oil fields where according to estimates, the volume of produced water by oil fields worldwide exceeds the oil by a factor of three. Subsequently, produced water (or water from oil production) represents one of the largest costs associated to the companies, since as a management strategy it is usually pumped or transported to outside treatment facilities, or pumped to the disposal wells. Moreover there are four main problems related to the microorganisms for this Sector: (I) biocorrosion; (II) contamination of the produced water which can lead to oil fields contamination after re-injection; (Ill) biological encrustation, which is the formation of biological deposits; and (IV) acidification, which is the production of hydrogen sulfide ($H_2S$) by bacteria.

With the expectation of high growth of produced water and public pressure resulting for regulation and controlling (Oliveira et al., 2012) is expected a high demand growth for laboratorial services (analysis) aiming at monitoring, controlling and characterization, as well as new ideas resulting in more efficient services.

Therefore there is a need to provide solutions allowing solving problems of water contamination at the regions where there is petroleum, however, with no presentation of a high risk to the environment or surrounding populations.

The search on prior art revealed some documents listed below but which does not reveal or suggest the present invention.

The document "In vitro evaluation of the antimicrobial activity of a castor oil-based irrigant" (Leonardo et al., *J. Endod.* 2001 Dez; 27(12):717-9.) refers to the antimicrobial activity of Endoquil (detergent solution of castor oil), 2% chlorhexidine gluconate solution and 0.5% NaOCl solution against gram positive bacteria and gram negative bacteria.

The document "Evaluation of the Antimicrobial and Phytochemical Properties of Oil from Castor Seeds (*Ricinus communis* Linn)" (Momoh et al., *Bull. Environ. Pharmacol. Life Sci.*; Volume 1 [10] Sep. 2012: 21-27) refers to antimicrobial evaluation and phytochemical properties of castor seed oil.

The document BR PI 0807634 reveals biocide compositions comprising at least one dialkyl amide and at least on biocide.

The document CN 102505497 reveals a method for preparation of a high durability antifouling and self-cleaning composition. This composition is polyurethane prepared from a mix comprising MDI and amino-modified silicone oil emulsion. However, this composition consists of petroleum derivates which can generate harmful by-products to the environment.

The document BR 10 2012 009648 A2 reveals a curable coating composition comprising organic hybrid networks of polyurethane-polysiloxane-Si, which has mechanical strength and antifouling property, that offers a solution to the problem of biofouling at marine environment. Antifouling coating is composed of at least one silane-terminated polyurethane, one silanol-terminated polysiloxane and possibly one or more polymeric binders, such as for example, epoxy and acrylic polymer. However, said composition among other technical reasons can bring environmental damage in addition to have complex and high-cost production process.

Thus, what is clear from literature researched, there are no documents found anticipating or suggesting the teachings of the present invention, and so that solution here proposed has novelty and inventive activity compared to the prior art.

BRIEF SUMMARY OF THE INVENTION

Thus, the present invention aims to solve constant problems at the prior art by methods for organisms control applying biocide compositions comprising castor oil and/or derivates.

In a first aspect, the present invention presents a method for bacteria control comprising a step of contact between a medium comprising bacteria and a biocide composition comprising from 30% to 60% by volume of ricinoleic acid, 30% to 60% by volume of castor oil and from 10% to 30% by volume of dialkylamine.

In a second aspect, the present invention presents a method for bacteria control comprising a step of contact between a medium comprising bacteria and a biocide composition comprising from 70% to 90% by volume of ricinoleic acid and from 10% to 30% by volume of dialkylamine.

In a third aspect, the present invention presents a method for fungi control comprising a step of contact between a medium comprising fungi and a biocide composition comprising from 40% to 100% by volume of ricinoleic acid, 0% to 60% by volume of castor oil and from 0% to 15% by volume of antifoaming.

In a fourth aspect, the present invention presents a method for virus control comprising a step of contact between a medium comprising virus and a biocide composition comprising from 40% to 100% by volume of ricinoleic acid and from 0% to 60% by volume of castor oil.

In a fifth aspect, the present invention presents a method for preventing encrustation on surfaces comprising an application on a surface of a composition comprising castor oil polyol and at least one diphenyl methane isocyanate, in which mass ratio of polyol and diphenyl methane isocyanate varies from 1:1 to 5:1.

In a sixth aspect, the present invention presents a method for preventing corrosion on surfaces comprising an application step on a surface of a composition comprising castor oil polyol and at least one diphenyl methane isocyanate, in which mass ratio of polyol and diphenyl methane isocyanate varies from 1:1 to 5:1.

Furthermore, the inventive concept common to all the claimed protection contexts is the use of biocide compositions comprising castor oil and/or derivates.

These and other aspects of the invention will be promptly estimated by skilled one and by companies with interest in the sector, and will be sufficient detailed described for its following reproduction.

BRIEF DESCRIPTION OF THE SEVERAL VIEWS OF THE DRAWINGS

In order to better define and clarify the content of the present patent application, the present figures are presented.

DETAILED DESCRIPTION OF THE INVENTION

Figure 1:
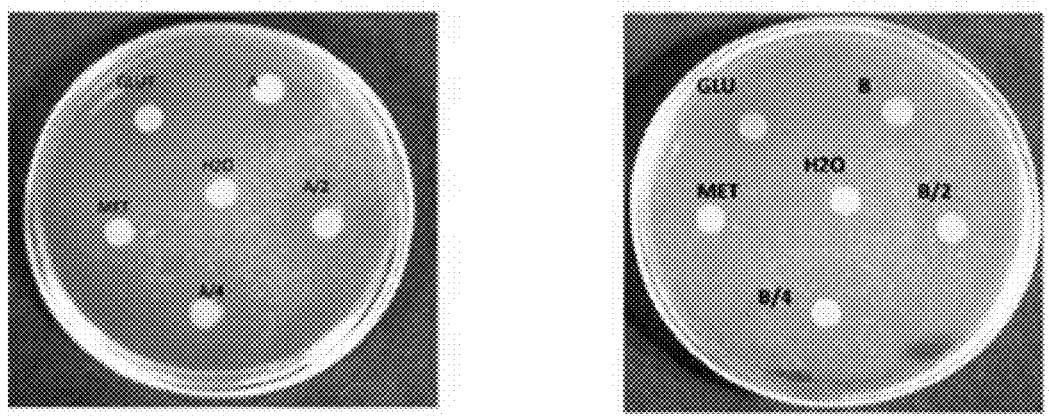
FIG. 1 shows experimental results obtained for disk diffusion method to qualitative analysis of biocide action at anaerobic bacteria #3. A=biocide HAB-1; B=biocide HAB-2; Glu=glutaraldehyde, Met=methanol, A=10 μL of biocide HAB-1 and B=10 μL of biocide HAB-2, A/2=5 μL of biocide HAB-1 e B/2=5 μL of biocide HAB-2 and A/4=2.5 μL of biocide HAB-1 e B/4=2.5 μL of biocide HAB-2.

The present invention describes the method of organisms control comprising biocide compositions comprising castor oil and/or derivates. The present invention can be used for controlling several microorganisms, such as bacteria, fungi and virus, in addition to controlling barnacles growth on surfaces, and for preventing corrosion on surfaces.

In one embodiment, the present invention can be used for controlling sulfate-reducing bacteria (BRS). Controlling of such bacteria is of great interest of oil industry since it is one of the responsible for the corrosion of drill bit and drilling equipments.

In a first aspect, the present invention presents a method for bacteria control comprising a step of contact between a medium comprising bacteria and a biocide composition comprising from 30% to 60% by volume of ricinoleic acid, 30% to 60% by volume of castor oil and from 10% to 30% by volume of dialkylamine.

In one embodiment, the composition comprises about 40% by volume of ricinoleic acid, about 40% by volume of castor oil and about 20% by volume of dialkylamine.

In one embodiment, the dialkylamine is diethanolamine.

In one embodiment, the castor oil is extracted from a cultivar selected from the group consisting of IAC-80, IAC-Guarani, IAC-226, IAC-2028.

In one embodiment, the method for bacteria control comprises a previous step of dilution of the biocide composition, wherein the biocide composition is diluted at a ratio of biocide composition to water of 1:10 to 1:1000.

In a second aspect, the present invention presents a method for bacteria control comprising a step of contact between a medium comprising bacteria and a biocide composition comprising from 70% to 90% by volume of ricinoleic acid and from 10% to 30% by volume of dialkylamine.

In one embodiment, the biocide composition comprises 80% by volume of ricinoleic acid and 20% by volume of dialkylamine.

In one embodiment, the dialkylamine is diethanolamine.

In one embodiment, castor oil is extracted from a cultivar selected from the group consisting of IAC-80, IAC-Guarani, IAC-226, IAC-2028.

In one embodiment, the method for bacteria control comprises a previous step of dilution of the biocide composition, wherein the biocide composition is diluted in a ratio of biocide composition to water of 1:10 to 1:1000.

In a third aspect, the present invention presents a method for fungi control comprising a step of contact between a medium comprising fungi and a biocide composition comprising from 40% to 100% by volume of ricinoleic acid, 0% to 60% by volume of castor oil and from 0% to 15% by volume of antifoaming.

In one embodiment, the composition comprises 2% by volume of antifoaming, 49% by volume of castor oil and 49% by volume of ricinoleic acid.

In one embodiment, the composition comprises 5% by volume of antifoaming, 47.5% by volume of castor oil and 47.5% by volume of ricinoleic acid.

In one embodiment, the composition comprises 10% by volume of antifoaming, 45% by volume of castor oil and 45% by volume of ricinoleic acid.

In one embodiment, the composition comprises 50% by volume of castor oil and 50% by volume of ricinoleic acid.

In one embodiment, the composition comprises 100% by volume of ricinoleic acid.

In one embodiment, the antifoaming is citric acid.

In one embodiment, the castor oil is extracted from a cultivar selected from the group consisting of IAC-80, IAC-Guarani, IAC-226, IAC-2028.

In one embodiment, the method for fungi control comprises a previous step of biocide composition dilution, wherein biocide composition is diluted in a ratio of biocide composition to water from 1:10 until 1:1000.

In a fourth aspect, the present invention presents a method for virus control comprising a step of contact between a medium comprising virus and a biocide composition comprising from 40% to 100% by volume of ricinoleic acid and from 0% to 60% by volume of castor oil.

In one embodiment, the composition comprises 50% by volume of ricinoleic acid and 50% by volume of castor oil.

In one embodiment, the composition comprises 100% by volume of ricinoleic acid.

In one embodiment, the castor oil is extracted from a cultivar selected from the group consisting of IAC-80, IAC-Guarani, IAC-226, IAC-2028.

In one embodiment, the method for virus control comprises a previous step of biocide composition dilution, wherein biocide composition is diluted in a ratio of biocide composition to water from 1:10 until 1:1000.

In a fifth aspect, the present invention presents a method for preventing encrustation on surfaces comprising application on a surface of a composition comprising castor oil polyol and at least one diphenyl methane isocyanate, wherein mass ratio of polyol and diphenyl methane isocyanate varies from 1:1 to 5:1.

In one embodiment, the mass ratio of polyol and diphenyl methane isocyanate varies from 2:1 to 3:1.

In one embodiment, the composition is a polyurethane.

In one embodiment, the composition comprises soybean oil polyol.

In one embodiment, the composition comprises mineral filling, pigment, sorbent, stabilizers, UV radiation filters, or combinations thereof.

In one embodiment, the composition comprises about 42% de castor oil polyol, about 33.4% of diphenyl methane isocyanate, about 20% of mineral filling, preferably dolomite, about 1% of pigment, preferably carbon black, about 1.5% of sorbent, preferably silica, about 0.0005% of stabilizer, preferably dibutyltin dilaurate, about 2% of UV radiation filter, preferably a titanium-based paste.

In one embodiment, the stabilizers are stabilizers of "pot life", that is, stabilizers of required time for composition double its viscosity. An important parameter to control the time that the composition remains suitable for use.

In one embodiment, the method for preventing encrustation prevents encrustation adhesion at ship hulls. In one embodiment, the composition can be used as dye.

In a sixth aspect, the present invention presents a method for preventing corrosion on surfaces comprising a step of applying on a surface a composition comprising castor oil polyol and at least one diphenyl methane isocyanate, wherein mass ratio of polyol and diphenyl methane isocyanate varies from 1:1 to 5:1.

In one embodiment, the mass ratio of polyol and diphenyl methane isocyanate varies from 2:1 to 3:1.

In one embodiment, the composition is a polyurethane.

In one embodiment, the composition comprises soybean oil polyol.

In one embodiment, the composition comprises mineral filling, pigment, sorbent, stabilizers, UV radiation filters, or combinations thereof.

In one embodiment, the composition comprises about 42% of castor oil polyol, about 33.4% of diphenyl methane isocyanate, about 20% of mineral filling, preferably dolomite, about 1% of pigment, preferably carbon black, about 1.5% of sorbent, preferably silica, about 0.0005% of stabilizer, preferably dibutyltin dilaurate, about 2% of UV radiation filter, preferably a titanium-based paste.

In one embodiment, the stabilizers are stabilizers of "pot life", that is, stabilizers of the required time for the composition double its viscosity. An important parameter to control the time that the composition remains suitable for use.

In one embodiment, the composition can be uses as waterproofing coating.

One advantage of the present invention is the use of plant oil (from castor bean and/or soybean, among other possible plant sources also) replacing petroleum derivates at the methods for preventing encrustation and corrosion, which brings savings to the manufacturing process and, for cases in which there is discharge of some material containing the composition, is possible to biodegrade without generating harmful byproducts to the environment. The blend of MDI's used acts as biocide agent inhibiting sulfate-reducing bacteria action and bacteria responsible for biocorrosion. This property replaces some heavy metals used for the same purpose in alternative products. By the simplicity of the components, is possible the manufacturing of large batches without high infrastructure investments. Thus, the manufacturing process is simple, with low costs, one of the factors for the low cost being the absence of petroleum derivates (which pass through a long and expensive distillation and cracking process).

The composition not only inhibits adherence of microorganism which will grow to form barnacles and reduces the sulfate-reducing bacteria action, but also creates protective sealing of metal isolating it from the contact with salty water and oxygen, both important factors of metal corrosion acceleration. The composition also has protective painting properties on steel, concrete and wood, with properties as: resistance to acids, as the sulfuric, nitric, hydrochloric, muriatic acid, among others, and resisting to temperatures up to 180° C.

In addition, the composition revealed by the present invention is inert and does not react with acid substances, being possible immediate application at tanks and pipelines such as, for example, tanks and pipelines of drinking water or wine. For example, tanks of ships carrying industrial water are also included for anticorrosive composition application.

As a viable option for controlling microorganisms or barnacles, more preferably for controlling BRS on oil drilling sites or for controlling barnacles growth on parts of the ships.

Definition of Some Terms/Expressions Used at Present Patent Application

Microorganism(s)

The term is intended, in the present patent application, as any kind of microorganism, such as for example, but not limited to: bacteria, fungi, virus, and protozoan, among others.

Bacteria BRS or BRS

The term is intended, in the present patent application, as being any genre or species of sulfate-reducing bacteria, that is, bacteria which can promote (chemical) reduction of sulphates to sulphides.

Dialkylamines

The term is intended, in the present patent application, as being secondary or tertiary amines replaced by at least two alkyl groups wherein alkyl groups can be linear, branched, substituted, functionalized or form rings. One not limiting example of dialkylamines are the dialcohols with secondary amine such as, for example, the diethanolamine (formula molecular $C_4H_{11}NO_2$) and which structural formula is following indicated by Formula I:

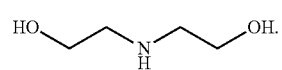

Formula I

Ricinoleic Acid

The term is intended, in the present patent application, as the 12-hydroxy-9-cis-octadecenoic acid (fatty acid omega-9) and represented by the Formula II below and, still at the context of the present patent application, ricinoleic acid can be obtained through different process such as, for example, saponification or fractional distillation of hydrolyzed castor oil.

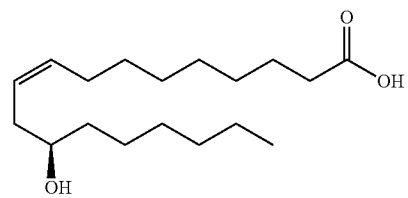

Formula II

Plaint Oils

The term, in the present patent application, refers to any oils from plant origin, for example, those found at castor bean (*Ricinus communis* L.) and/or soybean, among other. Among plant oils is also included linolenic acid.

Castor Oil

The term is intended, in the present patent application, as being the oil (extract) obtained from plant *Ricinus communis* or other varieties of same specie (cultivars). The castor oil can be obtained from the seeds of said plant. Castor oil is composed by 89.5 wt % of ricinoleic acid, 4 wt % of linolenic acid, 3 wt % of oleic acid, and other acids. Cultivars preferred are cultivars IAC-80, IAC-Guarani, IAC-226, IAC-2028.

Polyol

The term, in the present patent application, refers to any compound which has at least two hydroxyl (—OH) groups in the chain such as, for example, combination of two or more structures of ricinoleic acid (found at plants from genre *Ricinus*), or other acids present at plants from genre *Ricinus*, as 9,10-dihydrostearic acid, palmitic acid, stearic acid, oleic acid, linoleic acid, among others.

MDI

The term, in the present patent application, comprises any aromatic diisocyanate isomer, for example, chemical compound 4,4'-methylene diphenyl diisocyanate or diphenylmethane-4,4'-diisocyanate, among others.

Blend of MDI's

The term, in the present patent application, should be understood as being any combination of MDI's (abbreviation to several types of diphenyl methane isocyanate), such as diphenylmethane-4,4'-diisocyanate with any other MDI, at different ratios, among others.

Catalyst or Catalysts

The term, in the present patent application, refers to any blends of MDI or still a MDI at specific as, for example, but not limited to, the compound diphenylmethane-4,4'-diisocyanate.

Surface or Surfaces

The term, in the present patent application, refers to any surface on which living beings can come to settle, deposit, reproduce or colonize. The term comprises, but is not limited to, outer casings (hull) and interiors of any types of vessels, for example, boats and ships. The term also comprises any types of surfaces which can contact marine environment or any other type of environment containing water. It is also included reservoir and drinking water pipelines.

The term also comprises surfaces which can receive at least one waterproofing coating or ink layer such as, for example: slabs, roofs, surfaces of airplanes, spacecraft and other ways of space transportation, but not limited to such surfaces. In addition, the term also includes surfaces subjects to corrosion such as, for example, several metal surfaces, including from vessels and ways of air transport (airplanes, spacecraft, space probes, drones, among other air vehicles).

Produced Water

The term is intended, in the present patent application, as such is known at oil industry, that is: aqueous fluid of high salinity produced along with petroleum. It is about the biggest waste produced by the oil industry, and the failure of correct management of "produced water" is associated with environmental and health damages.

Antifoaming

In the context of the present patent application, the term "antifoaming" should be understood as any agent that reduces or prevent foaming as, for example, citric acid. The antifoaming is important, for example, but not limiting to, in applications as drilling fluid additive in the oil industry.

Brain Heart Infusion Medium

In the context of the present invention, the term should be understood as culture medium for microorganisms growth (example: bacteria) and containing, at its composition, brain and heart of different animal sources such as, for example: cattle, calf, among other mammals, as well as others compounds which constitute culture medium such as, for example, peptones, dextroses, among other. In one embodiment medium comprises yeast extract 0.5%, hemin 0.1% and menadione 0.1%.

Biocide HAB-1 or Biocide A

The term is intended, in the present patent application, as being a composition which is biocide, presenting activity to kill or inhibit proliferation of microorganisms, wherein the composition comprises 40% v/v of ricinoleic acid, 40% v/v of castor oil and 20% v/v of diethanolamine. Said biocide present biodegradability and low environmental toxicity (including animal toxicity).

Biocide HAB-2 or Biocide B

The term is intended, in the present patent application, as being a composition presenting activity to kill or inhibit proliferation of microorganisms, wherein the composition comprises: 80% v/v of ricinoleic acid and 20% v/v of diethanolamine. Said biocide presented several experimental results proving its biodegradability and its low environmental toxicity (including animal toxicity).

Percentages by Mass or by Volume

To better understanding the present invention, regarding compound quantities of compositions revealed at the present patent application, it should be understood that percentages of each compound are by mass (m/m) or by volume (v/v) regarding to the total mass or total volume of composition prepared. For example, if a composition presents at least 40% of castor oil and at least 40% of ricinoleic acid, it should be understood that said composition has at least 40% by mass (in relation to the total mass of the composition) of castor oil and at least 40% by mass (in relation to total mass of the composition) of ricinoleic acid. Taking the same example cited, it should understood that percentages also can refer to the volume and, at this understanding, it has at least 40% by volume (in relation to total volume of the composition) of castor oil and at least 40% by volume (in relation to total volume of the composition) of ricinoleic acid.

Proportion Between Polyol and MDI's Blend

In the context of the present patent application, when there is reference to proportion between polyol and MDI's blend, it should be understood that proportion, if not explicitly specified, should be understood as being proportion by weight/mass, by volume or still being stoichiometric amounts between polyol and MDI's blend.

EXAMPLES

Embodiments

Samples Collection of "Produced Water" and Cultivation of Bacterial Strains

Samples of produced water (50 ml) were collected for the group at a technical visit to mature basins at Bahia, Sergipe and Rio Grande do Norte aseptically. One sample was from water without treatment and the second was from the same water treated with a standard biocide. The samples were taken to the laboratory and the water was seeded on BHI (brain heart infusion) medium and cultured anaerobically. BHI medium was used because the tested bacteria have grown reproducibly at this medium, however other media could be employed, such as Postgate, yeast extracts, among other. BHI medium presented as an excellent medium for sulfate-reducing bacteria growth.

Antibacterial Effect

Two biocides fractions were used at this study and called BIOA (40% v/v of castor oil, 40% v/v ricinoleic acid and 20% v/v diethanolamine) and BIOB (80% v/v ricinoleic acid and 20% v/v diethanolamine). Aliquots of 500 µL from sulfate-reducing bacteria suspensions (108 UFC/ml) were seeded with Drigalski handle to obtains a uniform carpet of microbial growth at Petri plaques (90 mm of diameter) containing 20 ml of modified BHI Agar (yeast extract 0.5%, hemin 0.1% and menadione 0.1%).

Disk diffusion technique was used at Petri plaque, at appropriated conditions to bacterial growth. The results show this technique is sensitive and reliable and the results can be obtained at 24 hours.

Several species of anaerobic bacteria were tested, being the predominant species of the genre *Clostridium* as, for example: *Clostridium botulinum, Clostridium bifermentans, Clostridium sporogenes*, in addition to genre *Thalassospira*.

Samples of produced water collected after standard treatment did not show any bacterial growth and were not tested with the biocides. With the methodology described strict anaerobic bacteria were isolated called 3, 4 and 7 (genre *Clostridium* and *Thalassospira*) from produced water without treatment with the standard biocide.

To evaluate the biocides it was used a method in which disks made with paper Wattman number 1 (6 mm of diameter) were add aseptically on agar surface, after being previously soaked with substances biocides A and B at different volumes (A=10 µL, A/2=5 µL, A/4=2.5 µL and B=10 µL, B/2=5 µL and B/4=2.5 µL). Methanol and sterile distilled water solutions (used at biocides dilution) were used as negative control and 25% glutaraldehyde as positive control. Plaques were incubated for 24 hours at 37° C. in anaerobic environments.

Figure 2:
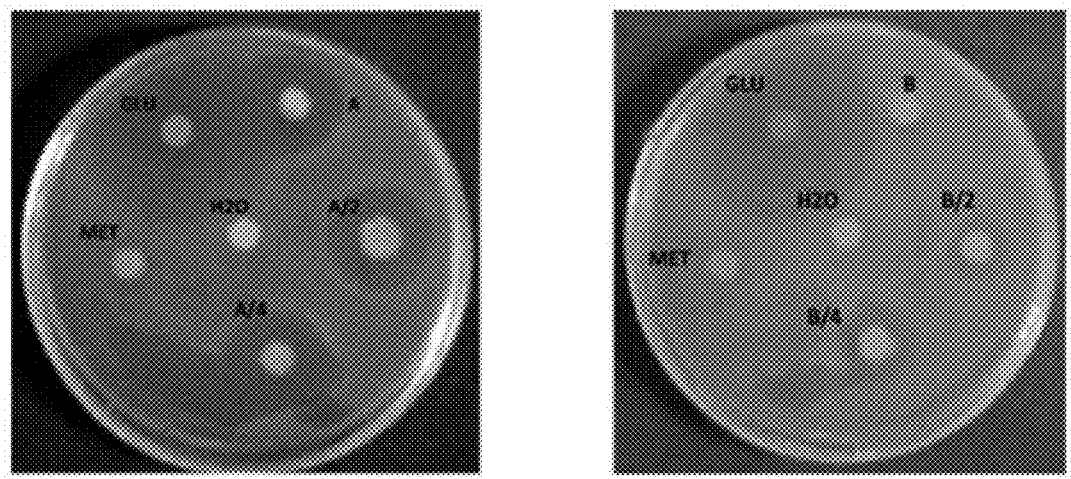
FIG. 2 shows experimental results obtained for disk diffusion method to quantitative analysis of biocides at anaerobic bacteria #4. A=biocide HAB-1; B=biocide HAB-2; Glu=glutaraldehyde, Met=methanol, A=10 μL of biocide HAB-1 and B=10 μL of biocide HAB-2, A/2=5 μL of biocide HAB-1 and B/2=5 μL of biocide HAB-2 and A/4=2.5 μL of biocide HAB-1 and B/4=2.5 μL of biocide HAB-2.
Figure 3:
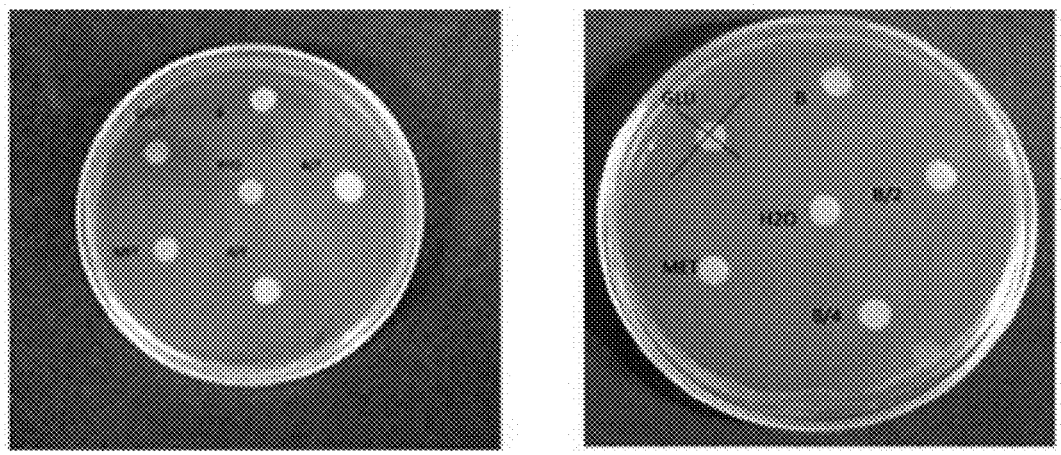
FIG. 3 shows experimental results of disk diffusion method to qualitative analysis of the biocides HAB action at anaerobic bacteria 7; A=biocide HAB-1; B=biocide HAB-2; Glu=glutaraldehyde, Met=methanol, A=10 μL of biocide HAB-1 and B=10 μL of biocide HAB-2, A/2=5 μL of biocide HAB-1 and B/2=5 μL of biocide HAB-2 and A/4=2.5 μL of biocide HAB-1 and B/4=2.5 μL of biocide HAB-2.
Figure 4:
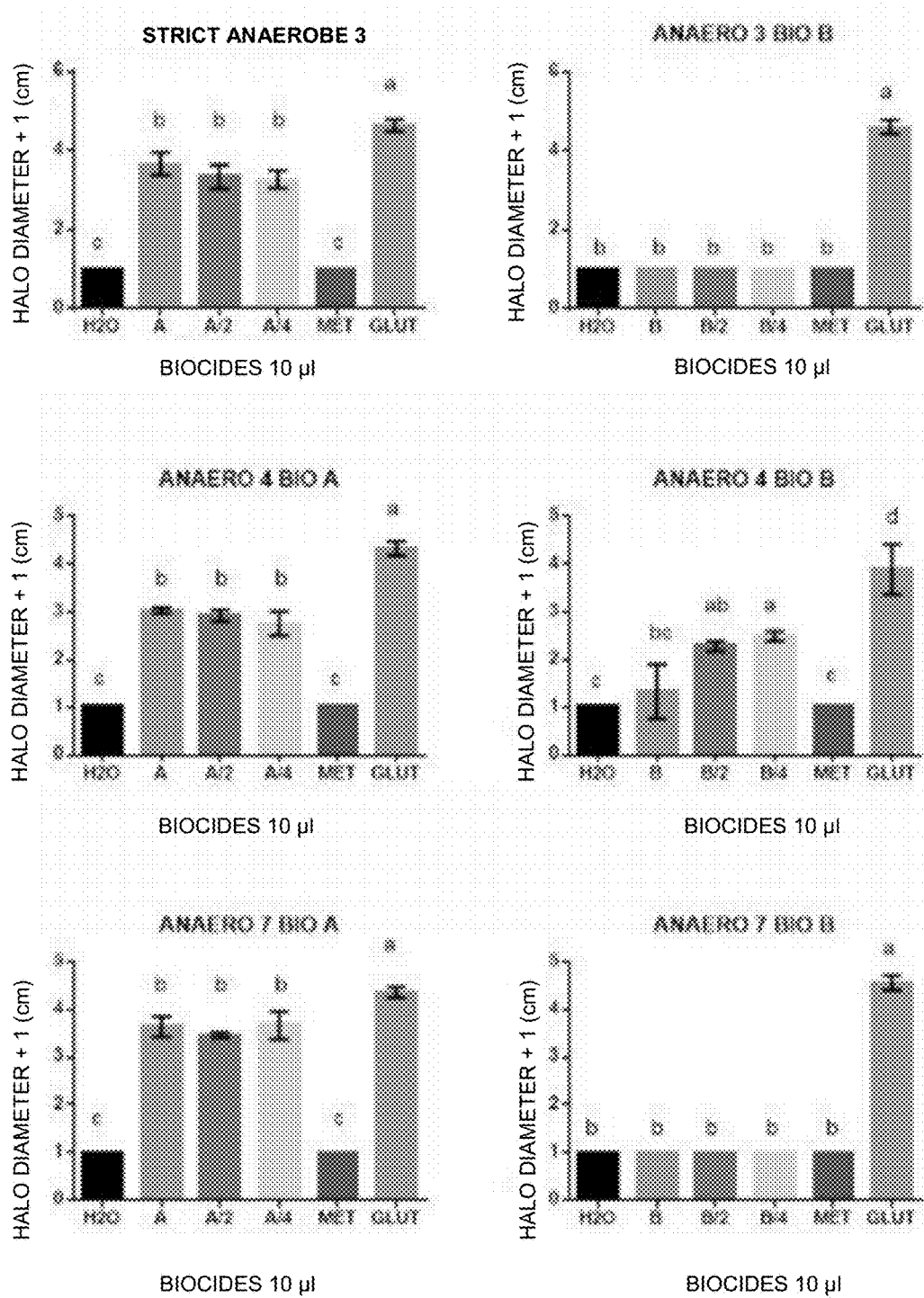
FIG. 4 shows the relationship between the halos diameter from the biocides and the controls.
Figure 5:
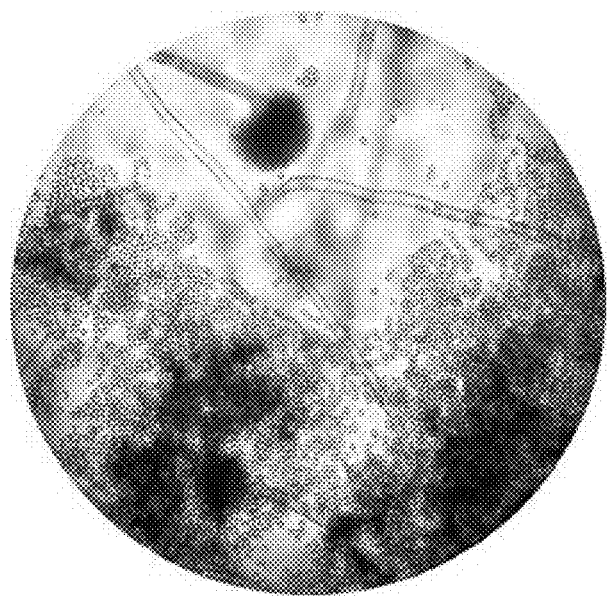
FIG. 5 shows powdery colony of *Aspergillus niger*, obverse white; verso dark, with many droplets and hyphae septated. Increase of 40×. Stained with KOH.
Figure 6:
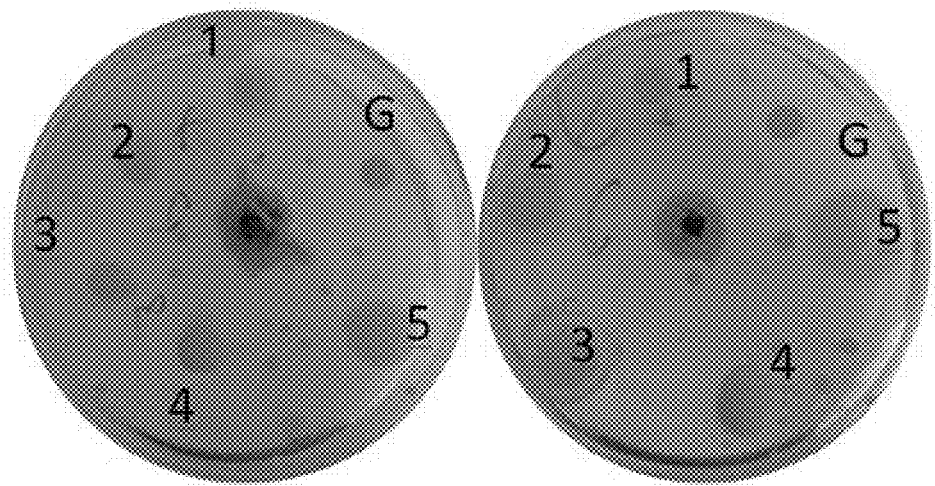
FIG. 6 shows the results of fungic growth inhibition (on *Aspergillus niger*) by compositions tested and indicated in Table 1.
Figure 7:
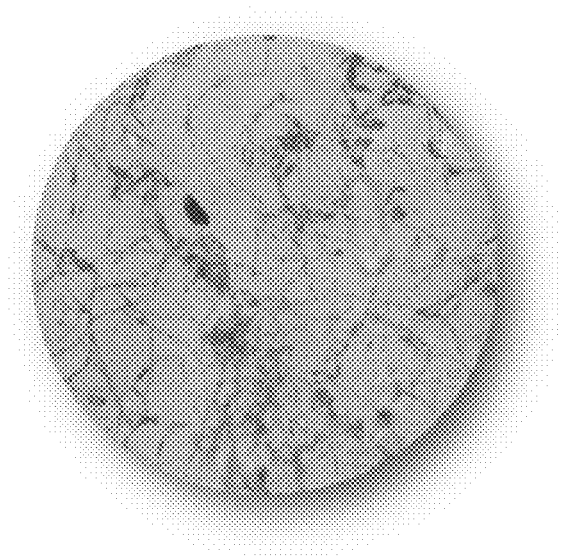
FIG. 7 shows powdery colony of hyaline fungi (bright) and with hyphae non septated of genre *Aspergillus*. Obverse white. Increase of 40×. stained with blue cotton.
Figure 8:
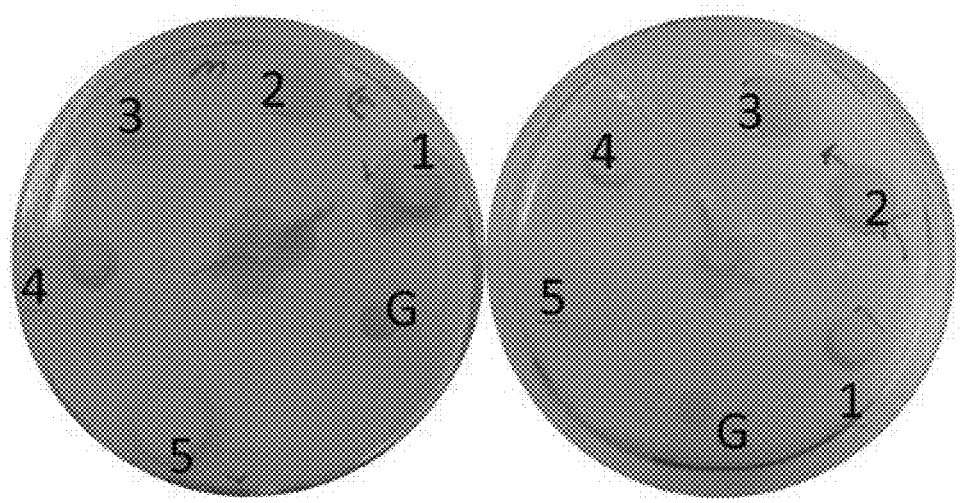
FIG. 8 shows the results of fungic growth inhibition by compositions tested and indicated in Table 1.

The biocide A and B were more efficient to all samples through view of inhibition halos (as can be seen at FIGS. 1, 2 and 3, where at left side it is biocide A and at right side it is biocide B). The relation of halo diameter and biocides concentration was statistically significant (FIG. 4). The biocide A was more efficient against all sample containing bacteria and also presented the technical advantage of having excellent solubility in water (pH 9-10) at ratios 1:1000, 1:100 and 1:10.

Thus, a composition (HAB-1) containing 40% of ricinoleic acid and 40% of castor oil, which presented as biodegradable and non toxic (to the environment and animals), is extremely efficient as biocide agent against isolated bacteria from samples of produced water from Mature Basins at Northeast of Brazil.

Antifungal Effect

To experimental tests at fungi from genre *Aspergillus*, were prepared Five (05) compositions, indicated as follow in following Table 1:

TABLE 1

Compositions tested at experimental tests with fungi from genre *Aspergillus*

| Composition # | Composition compounds (percentages by volume) |
|---|---|
| 1 | 2% citric acid; 49% castor oil; and 49% ricinoleic acid |
| 2 | 5% citric acid; 47.5% castor oil; and 47.5% ricinoleic acid |
| 3 | 10% citric acid; 45% castor oil; and 45% ricinoleic acid |
| 4 | 50% castor oil and 50% ricinoleic acid |
| 5 | 100% of ricinoleic acid |

To compositions tests indicated in Table 1, fungi were cultured in Agar Sabourand medium. After inoculation at Petri plaque, disks soaked with the compositions were added to the said Petri plaques and the same were incubated for 96 hours. The experimental results of tests for the compositions indicated in Table 1 in fungi show all compositions were efficient, presenting biocide effect, as indicated at FIGS. 5 to 8 (FIGS. 5 and 6 corresponding to the test performed at the specie *Aspergillus niger* and FIGS. 7 and 8 corresponding to test performed at other fungus from genre *Aspergillus*).

Antiviral Effect

To antiviral tests, the following compositions were tested: 50% castor oil and 50% de ricinoleic acid; and 100% de ricinoleic acid.

Figure 9:
FIG. 9 shows an image obtained by transmission electron microscopy to a virus control group at the experiments performed for biocide activity test of compositions indicated in Table 1.
Figure 10:
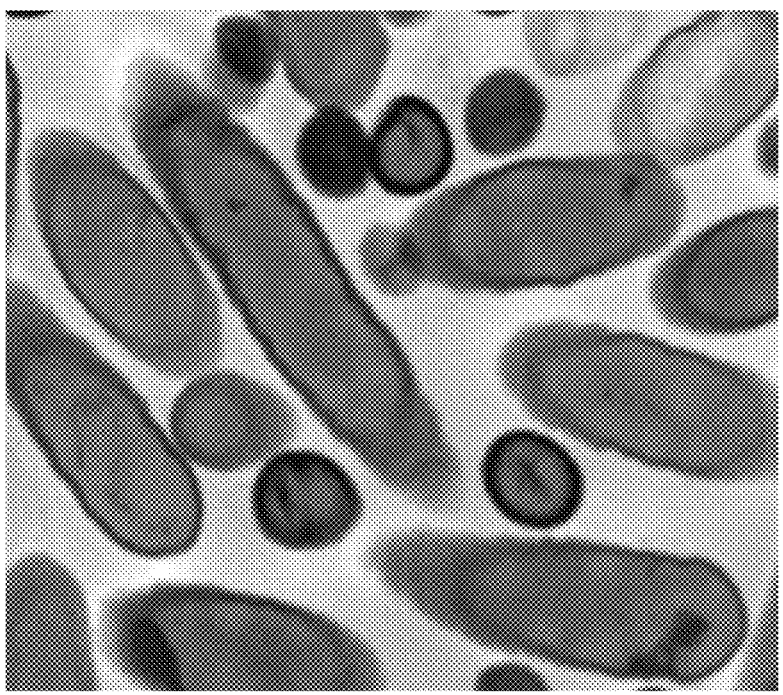
FIG. 10 shows an image obtained by transmission electron microscopy to other virus control group at the experiments performed for biocide activity test of compositions indicated in Table 1.
Figure 11:
FIG. 11 shows an image obtained by transmission electron microscopy to other virus control group at the experiments performed for biocide activity test of compositions indicated in Table 1.
Figure 12:
FIG. 12 shows an image obtained by transmission electron microscopy to a RNA virus group from family togaviridae, genre *Alphavirus* treated with compositions 50% castor oil/50% ricinoleic acid and 100% ricinoleic acid.
Figure 13:
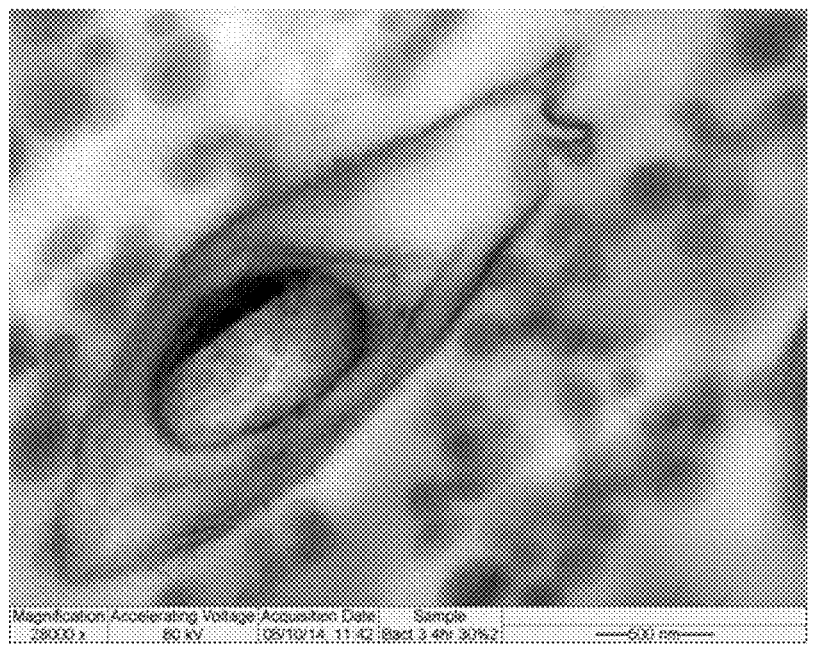
FIG. 13 shows other image obtained by transmission electron microscopy to a RNA virus group from family togaviridae, genre *Alphavirus* treated with compositions 50% castor oil/50% ricinoleic acid and 100% ricinoleic acid.
Figure 14:
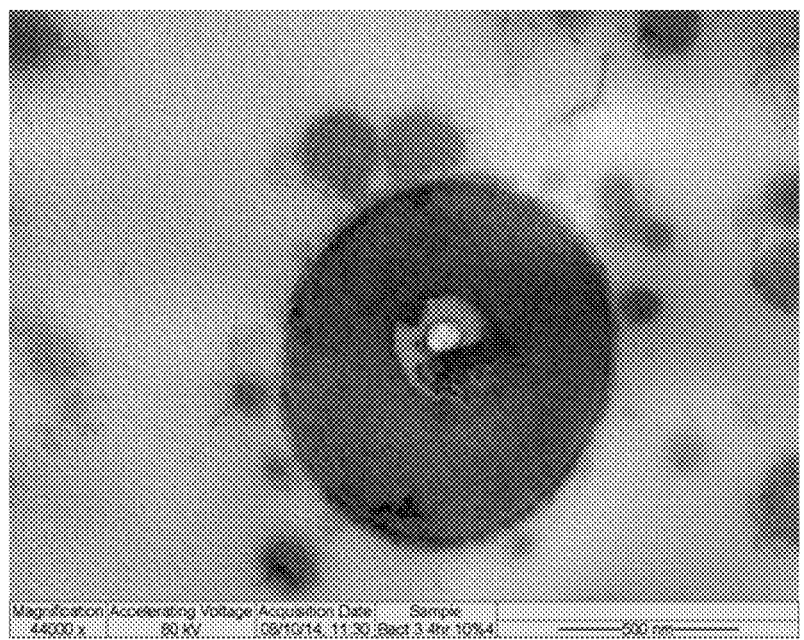
FIG. 14 shows other image obtained by transmission electron microscopy to a RNA virus group RNA from family togaviridae, genre *Alphavirus* treated with compositions 50% castor oil/50% ricinoleic acid and 100% ricinoleic acid.
Figure 15:
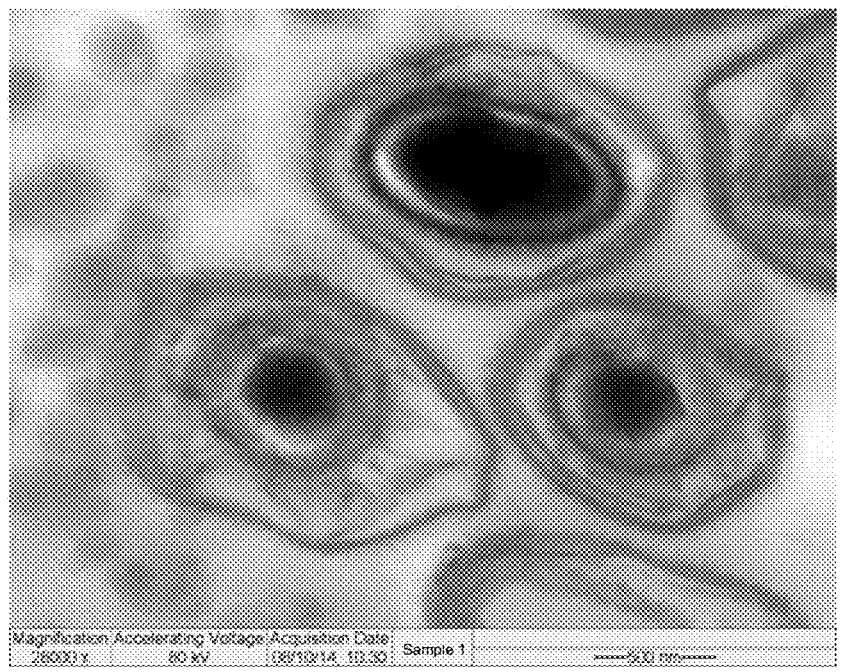
FIG. 15 shows other image obtained by transmission electron microscopy to a RNA virus group from family togaviridae, genre *Alphavirus* treated with compositions 50% castor oil/50% ricinoleic acid and 100% ricinoleic acid.

Said compositions were tested against a virus from genome RNA, which virus pertaining to the family Togaviridae, genre *Alphavirus*. Biocide showed antiviral activity at non toxic concentrations for mammalian cells culture as FIGS. 9 to 15, inhibiting above 90% of infectious viral particles at culture of treated cells (FIGS. 12 to 15) compared to a non treated control group (FIGS. 9 to 11).

Example of Composition Preparation Process

Composition preparation presented the step of adding, a reactor:
  500 mL of castor oil;
  500 mL of ricinoleic acid; and
  250 mL of diethanolamine;
it was obtained with the compound mix (castor oil, ricinoleic acid and diethanolamine) a isothermal reaction for a period of time of one hour and half to two hours. After this period of time it was obtained a composition with biocides properties (biocide A, in the case), as shown at the tests and experimental results.

Comparative Tests

Biocide compositions A and B were diluted at rate of 1:10, 1:100 and 1:1000 at tubes containing culture medium sodium thioglycollate and medium Postgate B. After dilution of the antimicrobial compounds bacterial consortia of *Dessulfovibrio alaskensis* (108 cell/ml) were added. Tubes were incubated for 20 days at 30° C. and antimicrobial activities were evaluated by turbity and production of $H_2S$, at medium thioglycollate, and by blackening of medium Postgate B. The positive control of antimicrobial activity used was THPS (Tetrakis sulfate (hydroxymethyl) phosphonium) and the negative control was consisted of inoculated culture medium with microorganisms.

Diluted compounds were tested on two different types of castor oil extracts. There were cellular consortia growth for media where were used two types of castor oils. There was inhibition when diluted biocides compounds of the present invention were used.

Therefore, biocides compounds of the present invention present surprising and higher results than the simple castor oil extracts.

TABLE 2

| Composition of medium Postgate B. | |
|---|---|
| Material | Quantity |
| Sodium Lactate (50% p/v) | 7 ml |
| Yeast Extract | 1 g |
| $KH_2PO_4$ | 0.5 g |
| $NH_4Cl$ | 1 g |
| $CaSO_4$ | 1 g |
| $Fe_2SO_4 \cdot 7H_2O$ | 0.5 g |
| Ascorbic Acid | 0.1 g |
| Sodium Thioglycollate | 0.1 g |
| $MgSO_4 \cdot 6H_2O$ | 2 g |
| NaCl | 35 g |
| Resazurin (0.025%) | 4 ml |
| Distilled water | 1000 ml |

Toxicity Test

Biocides A and B were also tested for toxicity at mammalian cells for human toxicity evaluation.

Vero Cells (kidney cells of African green monkey, ATCC CCL-81) were maintained at 37° C. with 5% of $CO_2$ at maintenance medium Eagle modified by Dulbeco (DMEM) supplemented with 10% of fetal bovine serum, 2 mM of L-glutamine, 10 mM of HEPES (pH 7.4) and non-essential amino acids (dilution 1:100 of non-essential amino acids, cat. #11140, Gibco). In order to performing the experiments, $3\times10^5$ cells/mL were cultured at plaques or cells culture bottles for 24 h, to reach confluence by means of trypsinization of confluent culture.

At this embodiment, the mixture to catalyze the ink refers to two parts of the said plant polyol of castor oil to one part of MDI (compound diphenylmethane-4,4'-diisocyanate).

Still referring to this embodiment, castor oil and soybean oil polyol is indicated as the following Formula III:

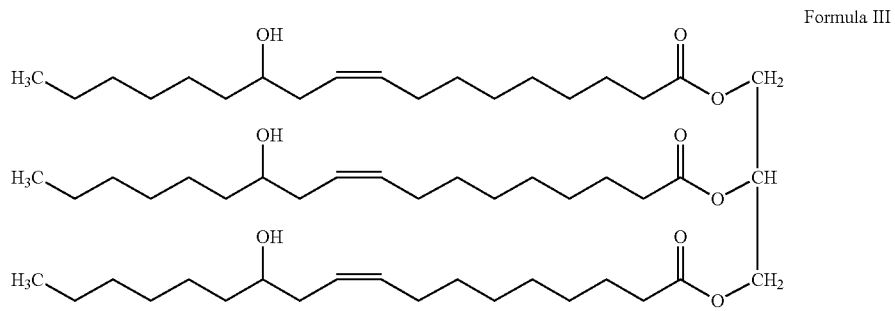 [SMILES: CCCCCCC(O)C/C=C\CCCCCCCC(=O)OCC(COC(=O)CCCCCCC/C=C\CC(O)CCCCCC)OC(=O)CCCCCCC/C=C\CC(O)CCCCCC]

Formula III

Cellular viability evaluation by neutral red incorporation method was performed according to Borenfreund and Purener (1985), with some changes. Briefly, culture of Vero cells confluents cultured at micro plaque of 96 wells was treated with serial dilutions of biocides substances for 24 h at 37° C. after incubation time, cell treatment medium was replaced to neutral red solution (50 μg/mL) for 3 h at 37° C. Cells were then fixed with formaldehyde 20% at PBS and neutral red incorporated by living cells was extracted with a methanol solution 50% and acetic acid 1%.

Figure 16:
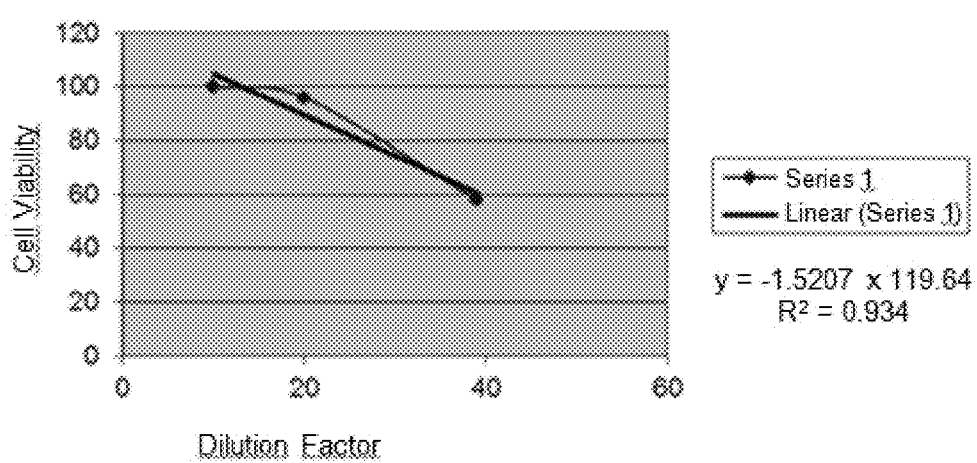
FIG. 16 shows a graph of toxicity test of biocide A against mammalian cells.
Figure 17:
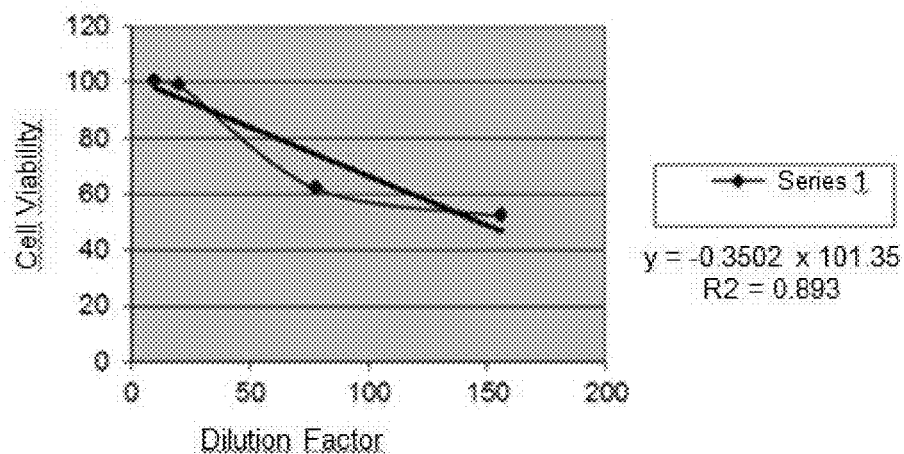
FIG. 17 shows a graph of toxicity test of biocide B against mammalian cells.

Absorbance reading was performed at λ 490 nm. Absorbance of non-treated cells was considered 100% of viability and substances dilutions in which 50% of cells were viable ($CC_{50}$%) were established by linear regression (FIGS. 16 and 17). To biocide A, $CC_{50}$% was of 45.79±3.2, and to biocide B was of 239.4±26.3. Therefore both biocides are non toxic at concentrations used at the present invention.

Formula III shows structure of the ricinoleic acid triglycerol.

Following Formula IV indicates one of the castor oil components.

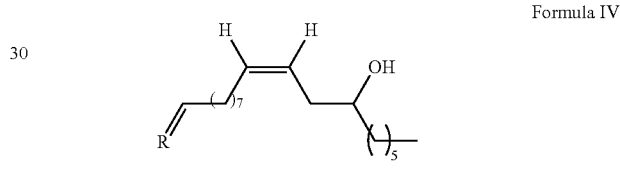

Formula IV wherein R at the Formula IV comprises any type of chain containing carbon atoms, being branched or non-branched.

In one more embodiment, the composition comprises plant polyol based on castor oil. Said composition comprises also 30% of mineral filling, 1.5% of pigment based on carbon black (this quantity varies according to desired shade), moisture absorber 2% (sorbent), catalyst based on tin to regulate "pot life", and a paste based on titanium dioxide, about 3%. The mixture ratio to catalysis said composition is of 2 parts of polyol (composition described above) and 1 part of MDI (diphenylmethane-4,4'-diisocyanate). However, other ratios between polyol and MDI were also tested such as, for example: 1.5 parts of polyol to 1 part of MDI and also 4 parts of polyol to 1 part of MDI, as indicated in following table 4:

Composition with Antifouling Effect (or Anti-Crackling) and Anticorrosive Effects One of the embodiments of the composition revealed at the present patent application presents the following components, as indicates in the following Table 3:

TABLE 3

Components of composition developed at this embodiment

| Component | Component function at the composition/ mix | Percentage (in relation to the total by weight) |
|---|---|---|
| Castor oil polyol | Antifouling action | 63.5% |
| Dolomite (mineral filling) | Texture and ink thixotropy | 30% |
| Carbon black (pigments) | Pigment | 1.5% |
| Silica | Moisture absorber (sorbent) | 2% |
| Tin catalyst (dibutyltin dilaurate) | Time control of pot life | 0.001% |
| titanium-based paste | Anti-UV | 3% |

Tin catalyst, in one of the embodiments presented at this patent application, is dibutyltin dilaurate. However, other catalysts based on tin are perfectly applicable such as, for example, tin octanoate. Replacement of tin catalyst did not change the characteristics of the final product obtained.

TABLE 4

Ratio between polyol (plant polyols of castor oil) and MDI (diphenylmethane-4,4'-diisocyanate)

| Polyol (plant polyols of castor oil) | MDI (4,4'-diphenylmethane diisocyanate, # CAS 9016-87-9) |
|---|---|
| 1 part | 1 part |
| 1.5 parts | 1 part |
| 2 parts | 1 part |
| 3 parts | 1 part |
| 4 parts | 1 part |

Among plant oil constituents, soybean oil contains linolenic acid and castor oil contains the compound represented by formula III. However, it should be understood that it is just one of the constituents found at soybean oil and castor oil (especially in regard to the unsaturations present at carbon chain), therefore encompassing others constituents of plant oils.

All components previously mentioned can be replaced for other components presenting the same function, no impairing final proprieties of the composition. Thus, components function is following explained: mineral filling is a dolomite used to give texture and ink thixotropy; pigment is carbon black, used to give color; silica is used to adsorbs moisture (sorbent) from polyol; paste based on titanium dioxide acts as UV (ultraviolet rays) barrier to preventing material destruction; MDI or its blends function is to catalysis the reaction and form the polymer with totally inert molecules, that is, once catalyzed, it not react with external environment Both aliphatic inks and aromatic inks were tested, being: aliphatic inks more stable, without suffering color change over time; and aromatic inks, those inks having aromatic compounds in its composition, making color more yellowing over time.

Polyol of the present invention embodiment presented the following technical characteristics: density about 1.1 kg/m$^3$, pH about 6.5 and about 7.5 and characteristic odor of plant oil, in addition to having light gray color.

Figure 18:
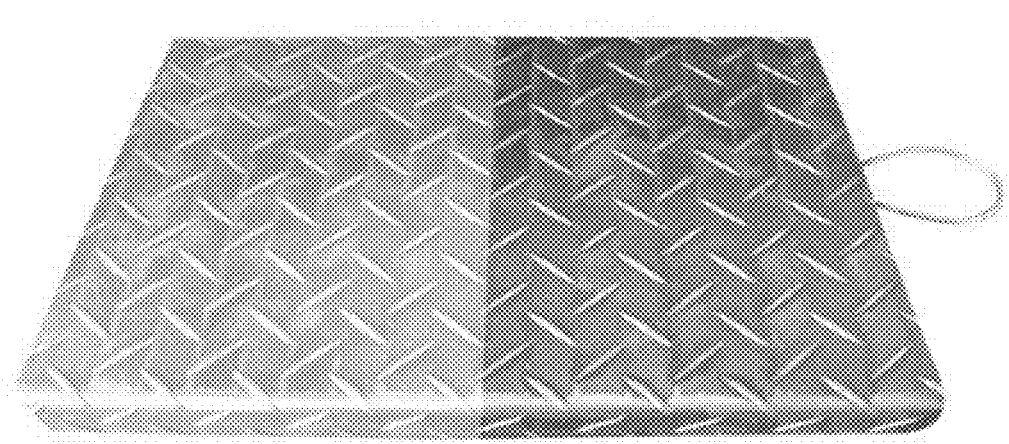
FIG. 18 shows a plate wherein there was application of composition on half of it (left side) and, on the other one, there was no application (right side).

Composition of the present embodiment was applied at half metal plaque, as FIG. 18 (left side is the side on which composition was applied). Metal plaque was then submerged in a river for 4 years.

Figure 19:
FIG. 19 shows the same plaque referred at FIG. 1 after four (4) years immersed in the aquatic environment.

After 4 years, the plaque was recovered and it was possible to verify there was encrustation only at the right side of the plaque (according to the FIG. 19), proving composition efficacy on preventing encrustation on surfaces.

Production Process

In one embodiment, it was initiated the polyol production with 600 liters of castor oil, the remaining components being added on top of this oil volume. It is put 120 kg of mineral filling, 12 liters of soybean oil and 10 to 15 kg of moisture adsorbent (sorbent), and it is added a paste composed of titanium dioxide, about 20 liters. The catalyst is 100% of its volume of diphenylmethane-4 4'diisocyanate.

In other embodiment, it was initially put on the reactor 600 liters of castor oil. It was added 12 liters of soybean oil. It was put 120 kg of dolomite and the components were mixed by reactor beater. It was added 20 liters of paste based on titanium dioxide. During 1 hour and 30 minutes the added components were mixed through gear pump for total homogenization. This description was for the polyol production. For MDI production, it was fractioned into packaging of 5 liters.

Tests and Experimental Results of Composition Anticorrosive Effects Developed from Exemplar Embodiment Composition revealed at the present invention was tested on stainless steel flexible hoses present in launchers rocket/shuttles, different tests being performed for corrosion strength evaluation at an artificial environment: test performed at 5% of sodium chloride (NaCl) for until two thousand (2000) hours and a test for reactivity evaluation on propellant rocket/chemical fuels applied to the composition tested and revealed at the present patent application.

Figure 20:
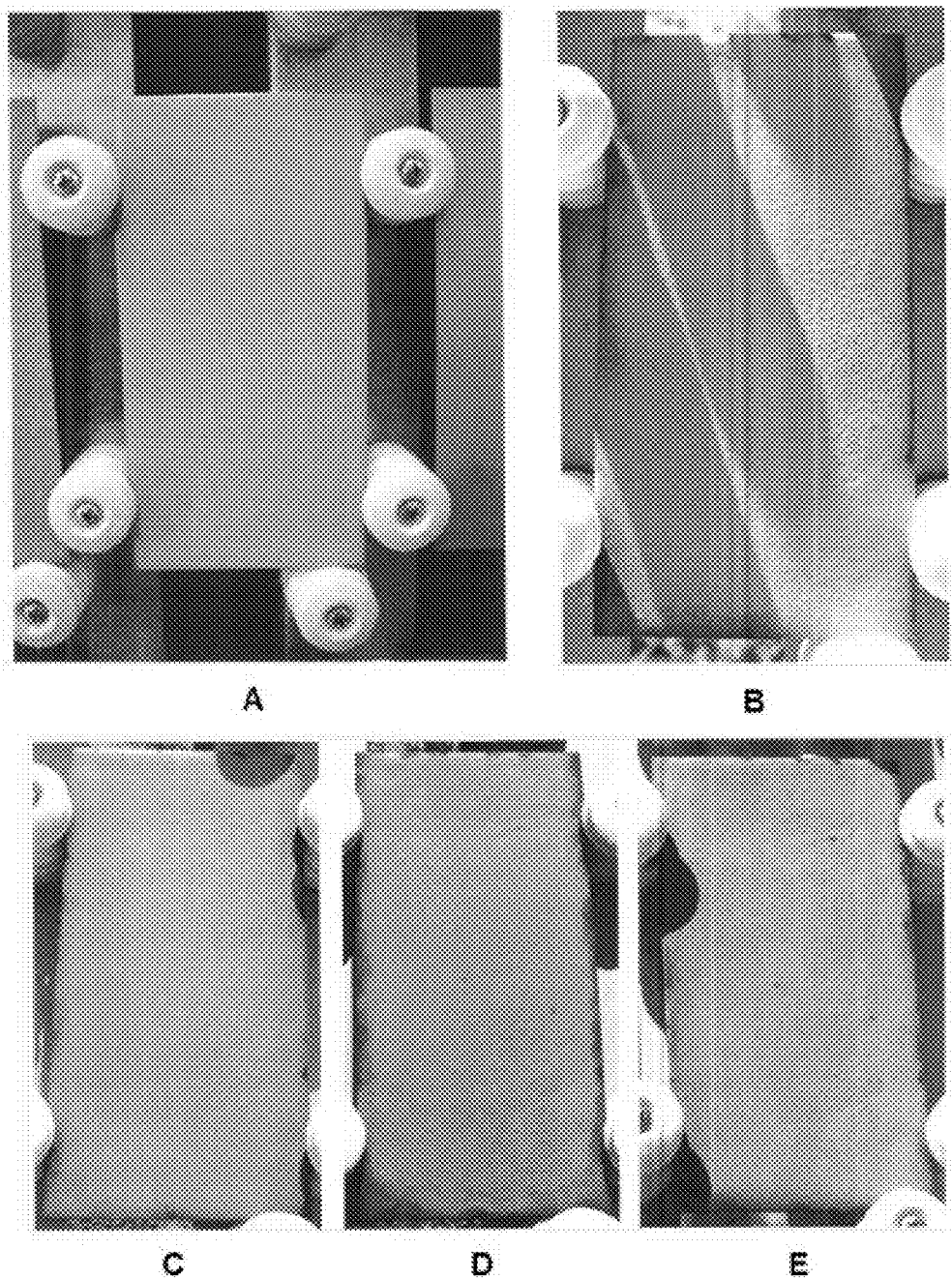
FIG. 20 shows the results of surface exposure treated with the composition revealed by the present invention to the test corrosion effects at center of corrosion experiments of National Aeronautics and Space Administration (NASA).
Figure 21:
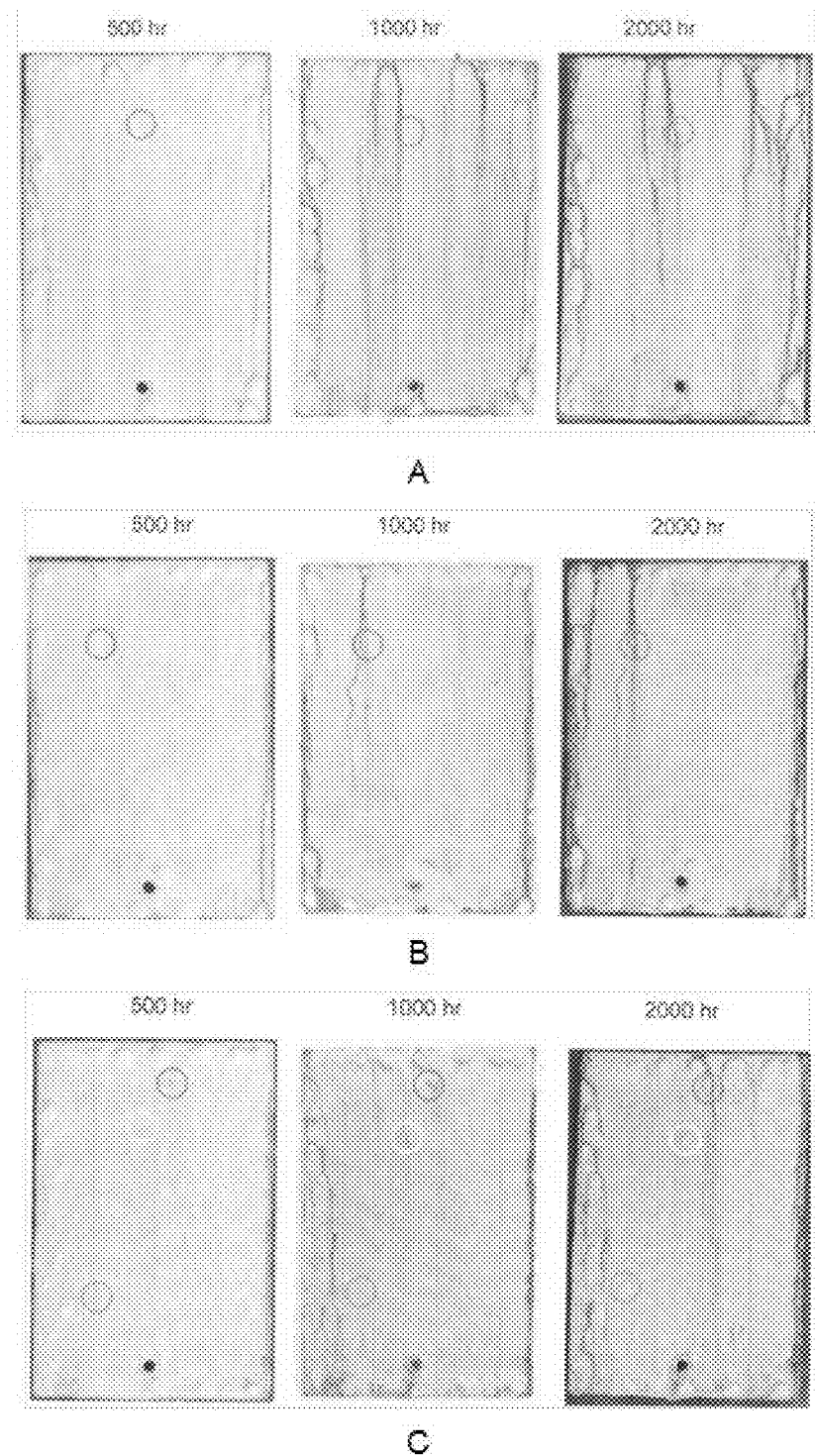
FIG. 21 shows the anticorrosive results obtained by the composition revealed at the present invention (test according to rule ASTM B117—Salt Fog Test) at the center of experiments for corrosion of the National Aeronautics and Space Administration (NASA).
Figure 22:
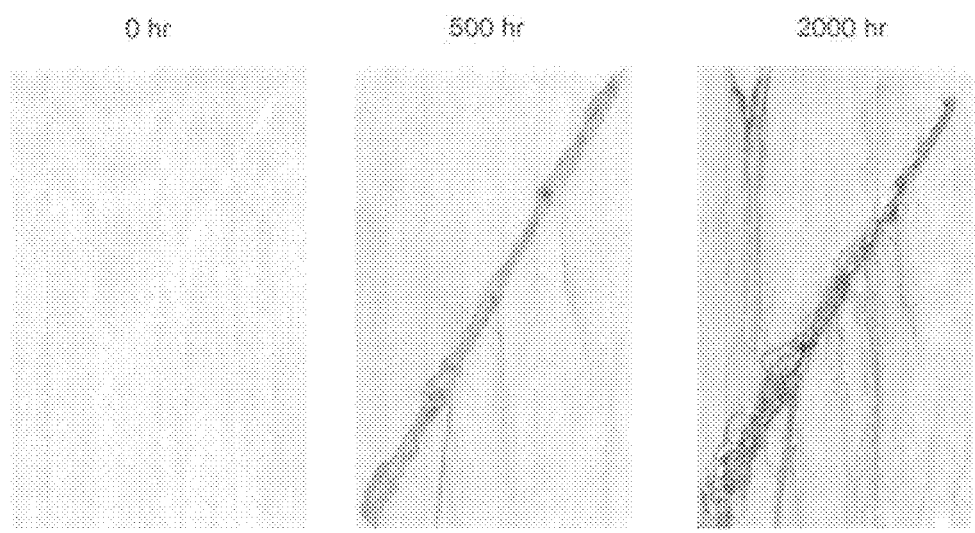
FIG. 22 shows the anticorrosive results obtained by the composition revealed at the present invention (test according to rule ASTM B117—Salt Fog Test) at the center of experiments for corrosion of the National Aeronautics and Space Administration (NASA).

Said anticorrosion tests were conducted before the National Aeronautics and Space Administration (NASA), the performed tests were: of ASTM D2370-98 (evaluation test on corrosion strength in an artificial environment); D4060-07 test (abrasion strength); and D4541-02 test (force). FIGS. 20 to 22 of the present patent application illustrate in details the results obtained on the corrosion tests with the composition which is revealed by the present patent application.

The test results show that the composition object of this patent application proved to be very suitable and even exceeding initial expectations, the experiments being conducted at the "NASA's Corrosion Technology Laboratory Beachside Atmospheric Exposure Test Facility".

The results on the composition reactivity test revealed are indicated in the following table (Table 5) compared to chemical agents with propellants/oxidative substances (chemical compounds MMH, $N_2H_4$ and $N_2O_4$). Tests with temperature increase lower than 2.8° C. were approved.

TABLE 5

Results obtained for anticorrosive composition tested.

| Chemical compound | Temperature increase | Notes |
|---|---|---|
| MMH | 1.6° C. for 10 min | Delaminated |
| $N_2H_4$ | 0.7° C. for 2 min | None |
| $N_2O_4$ | None | Rough, Delaminated |

Thus, the present invention reveals surprising antifouling and anticorrosive effects of polyols from castor oil in combination with MDI's blend.

Those skilled in the art will appreciate the knowledge presented herein and they could reproduce the invention at the modalities presented and other variants within the scope of appended claims.

What is claimed is:

1. A method for bacteria control, comprising a step of contact between a medium comprising bacteria and a biocide composition comprising from 30% to 60% by volume of ricinoleic acid, from 30% to 60% by volume of castor oil, and from 10% to 30% by volume of dialkylamine.

2. The method for bacteria control according to claim 1, wherein the biocide composition comprises about 40% by volume of ricinoleic acid, about 40% by volume of castor oil, and about 20% by volume of dialkylamine.

3. The method for bacteria control according to claim 1, wherein the dialkylamine is diethanolamine.

4. The method for bacteria control according to claim 1, wherein the castor oil is extracted from a cultivar selected from the group consisting of IAC-80, IAC-Guarani, IAC-226, IAC-2028.

5. A method for bacteria control, comprising a step of contact between a medium comprising bacteria and a biocide composition comprising from 70% to 90% by volume of ricinoleic acid and from 10% to 30% by volume of dialkylamine.

6. The method for bacteria control according to claim 5, wherein the biocide composition comprises 80% by volume of ricinoleic acid and 20% by volume of dialkylamine.

7. The method for bacteria control according to claim 5, wherein the dialkylamine is diethanolamine.

8. The method for bacteria control according to claim 5, wherein the castor oil is extracted from a cultivar selected from the group consisting of IAC-80, IAC-Guarani, IAC-226, IAC-2028.

9. The method for bacterial control according to claim 1, wherein the bacteria is a sulfate-reducing bacteria.

10. The method for bacterial control according to claim 5, wherein the bacteria is a sulfate-reducing bacteria.

\* \* \* \* \*